United States Patent
Mashima et al.

(10) Patent No.: US 7,635,776 B2
(45) Date of Patent: Dec. 22, 2009

(54) LIGANDS AND COMPLEX COMPOUNDS CONTAINING THE SAME

(75) Inventors: Kazushi Mashima, Ikeda (JP); Koji Ohno, Osaka (JP); Kazuhiko Matsumura, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 736 days.

(21) Appl. No.: 10/542,659

(22) PCT Filed: Feb. 4, 2004

(86) PCT No.: PCT/JP2004/001146

§ 371 (c)(1),
(2), (4) Date: Sep. 8, 2005

(87) PCT Pub. No.: WO2004/069786

PCT Pub. Date: Aug. 19, 2004

(65) Prior Publication Data

US 2006/0111572 A1      May 25, 2006

(30) Foreign Application Priority Data

Feb. 6, 2003   (JP) .............................. 2003-030067

(51) Int. Cl.
C07C 211/00   (2006.01)
C07F 15/00    (2006.01)
(52) U.S. Cl. ..................... 546/2; 548/101; 556/137; 564/368
(58) Field of Classification Search ............... 546/2; 548/101; 556/137; 564/368
See application file for complete search history.

(56) References Cited

U.S. PATENT DOCUMENTS 3,098,841 A * 7/1963 Morris et al. ............... 524/222

FOREIGN PATENT DOCUMENTS

| JP | 2000-256384 | 9/2000 |
| JP | 2002-363143 | 12/2002 |

OTHER PUBLICATIONS

D. A. Evans et al., "A Chiral Samarium-Based Catalyst for the Asymmetric Meerwein-Ponndorf-Verley Reduction", J. Am. Chem. Soc., vol. 115, pp. 9800-9801, 1993.

B. M. Trost et al., "Asymmetric Aldol Reaction via a Dinuclear Zinc Catalyst: α-Hydroxyketones as Donors", J. Am. Chem. Soc., vol. 123, pp. 3367-3368, 2001.

M. Su Han et al.,"Naked-Eye Detection of Phosphate Ions in Water at Physiological pH: A Remarkably Selective and Easy-To-Assemble Colorimetric Phosphate-Sensing Probe", Angew. Chem. Int. Ed., vol. 41, No. 20, pp. 3809-3811, 2002.

M. Orama et al., "Formation of Copper(II), Cobalt(II), Zinc(II) and Lead(II) Complexes N, N, N', N'-Tetrakis(2-hydroxypropyl)-ethylenediamine in Aqueous Solution", Finn. Chem. Lett., No. 6, pp. 182-185, 1979.

J. Gao et al., "Asymmetric cyclopropanation catalyzed by $C_2$-symmetric bis-(ephedrine)-Cu(II) complexes", Journal of Molecular Catlaysis A: Chemical, vol. 191, No. 1, pp. 23-27, Jan. 2, 2003.

D. A. Evans et al., "A Chiral Samarium-Based Catalyst for the Asymmetric Meerwein-Ponndorf-Verley Reduction", Journal of the American Chemical Society, vol. 115, No. 21, pp. 9800-9801, 1993.

K. Ohno et al., "Asymmetric Transfer Hydrogenation of Aryl Ketones Catalyzed by Salt-Free Two Samarium Centers Supported by a Chiral Multidentate Alkoxy Ligand", Organic Letters, vol. 6, No. 25, pp. 4695-4697, 2004.

* cited by examiner

*Primary Examiner*—Porfirio Nazario Gonzalez
(74) *Attorney, Agent, or Firm*—Wenderoth, Lind & Ponack, L.L.P.

(57) ABSTRACT

A ligand represented by the formula (1):

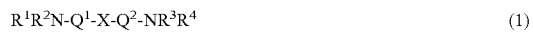

$$R^1R^2N\text{-}Q^1\text{-}X\text{-}Q^2\text{-}NR^3R^4 \qquad (1)$$

wherein $R^1$, $R^2$, $R^3$ and $R^4$ are each the same or different and represent a group represented by the formula (2):

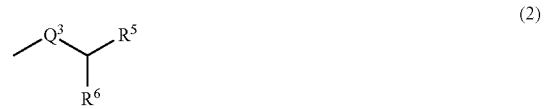

(2)

wherein $Q^3$ is an optionally substituted alkylene group, an optionally substituted cycloalkylene group, an optionally substituted arylene group, or an optionally substituted divalent heterocyclic group, $R^5$ is an optionally substituted alkyl group, an optionally substituted aryl group or an optionally substituted heterocyclic group and $R^6$ is a substituent which may coordinate or bind to a metal atom, or $R^5$ and $R^6$, taken together, may form a ring, $Q^1$ and $Q^2$ are each the same or different and represent an optionally substituted alkylene group or a single bond, and X is a divalent spacer.

14 Claims, No Drawings

LIGANDS AND COMPLEX COMPOUNDS CONTAINING THE SAME

This application is a U.S. national stage of International Application No. PCT/JP2004/001146 filed Feb. 4, 2004.

TECHNICAL FIELD

The present invention relates to a ligand, its complex compound and a method for the production of the same.

BACKGROUND ART

Up to now, complex compounds prepared by coordinating or binding various ligands to metal atoms, have been used as a catalyst for various chemical reactions such as asymmetric hydrogenation, asymmetric transfer hydrogenation, asymmetric hydrosilylation, asymmetric Heck reaction, asymmetric aldol reaction, asymmetric ene reaction, asymmetric oxidation, asymmetric epoxidation, asymmetric Diels-Alder reaction, polymerization, and the like (cf. JP-A-2000-256384, JP-A-2002-255985, JP-A-2002-363143, J. Am. Chem. Soc., 2001, 123, 3367-3368, and J. Am. Chem. Soc., 1993, 115, 9800-9801).

These days, in the field of chemical industry, appearance of a catalyst with an excellent catalytic activity has been strongly desired and a lot of researches have been carried out therefor. It is generally considered that a less amount of excellent catalysts catalyzes the chemical reactions to give objective compounds in a high yield and enantioselectivity.

DISCLOSURE OF THE INVENTION

The technical problem of the present invention is to provide a novel ligand and a complex compound containing said ligand as a constituent element. More particularly, the problem of the present invention resides in providing complex compounds which, when used as a catalyst in the chemical reactions mentioned above, show an excellent catalytic characteristics, more specifically such as excellent yield and enantioselectivity, and excellent catalytic activities, and to provide a ligand for such complex compounds.

The present inventors have studied intensively to solve the problems mentioned above, and have found that a ligand represented by the formula (1):

(wherein $R^1$, $R^2$, $R^3$ and $R^4$ are each the same or different and represent a group which is represented by the formula (2):

wherein $Q^3$ is an optionally substituted alkylene group, an optionally substituted arylene group, or an optionally substituted divalent heterocyclic group; $R^5$ is an optionally substituted alkyl group, an optionally substituted aryl group or an optionally substituted heterocyclic group; $R^6$ is a substituent which may coordinate or bind to a metal atom, or $R^5$ and $R^6$, taken together, may form a ring; $Q^1$ and $Q^2$ are each the same or different and represent an optionally substituted alkylene group or a single bond; and X is a divalent spacer), and a complex compound formed from the said ligand and metal atom can solve the problems mentioned above. The present inventors have further investigated extensively based on these findings and completed the present invention.

Namely, the present invention relates to:

(1) a ligand represented by the formula (1):

wherein $R^1$, $R^2$, $R^3$ and $R^4$ are each the same or different and represent a group represented by the formula (2):

wherein $Q^3$ is an optionally substituted alkylene group, an optionally substituted cycloalkylene group, an optionally substituted arylene group, or an optionally substituted divalent heterocyclic group; $R^5$ is an optionally substituted alkyl group, an optionally substituted aryl group or an optionally substituted heterocyclic group; and $R^6$ is a substituent which may coordinate or bind to a metal atom, or $R^5$ and $R^6$, taken together, may form a ring;

$Q^1$ and $Q^2$ are each the same or different and represent an optionally substituted alkylene group or a single bond; and X is a divalent spacer.

The present invention also relates to:

(2) the ligand according to the above (1), characterized in that the ligand is an optically active compound, (3) the ligand according to the above (1), characterized in that no asymmetric carbon atom is present in the formula (2), (4) the ligand according to any one of the above (1) to (3), characterized in that the spacer is an optionally substituted alkylene group, an optionally substituted arylene group or an optionally substituted divalent heterocyclic group, and (5) the ligand according to any one of the above (1) to (4), characterized in that the length of $Q^1$-X-$Q^2$ is from 2 to 30 angstroms.

The present invention also relates to:

(6) the ligand according to any one of the above (1) to (5), characterized in that $Q^3$ is an alkylene group of 1 to 6 carbon atoms, (7) the ligand according to any one of the above (1) to (6), characterized in that $R^5$ is an aryl group, (8) the ligand according to any one of the above (1) to (7), characterized in that $R^6$ is a hydroxy group, an alkoxy group of 1 to 6 carbon atoms, an amino group or a substituted amino group, and (9) the ligand according to any one of the above (1) to (6), characterized in that the ring formed when $R^5$ and $R^6$ are taken together is an oxazoline, a pyrrolidine or a piperidine.

The present invention also relates to:

(10) a complex compound characterized by containing, as a constituent element, the ligand according to any one of the above (1) to (9) and a metal atom,

(11) the complex compound according to the above (10), characterized in that the metal atom belongs to any one of groups 3 to 14 of the periodic table,

(12) the complex compound according to the above (10) or (11), characterized in that the metal atom is lanthanum, samarium, titanium, zirconium, vanadium, rhenium, iron, ruthenium, cobalt, rhodium, iridium, nickel, palladium, copper, zinc, aluminum, tin, gold, silver or platinum,

(13) use of the ligand described in any one of the above (1) to (9) for the production of the complex compound described in any one of the above (10) to (12), and

(14) use of the complex compound described in any one of the above (10) to (12) as a catalyst for asymmetric synthesis reactions.

The present invention also relates to:

(15) a method for producing a compound of the formula (1):

$$R^1R^2N\text{-}Q^1\text{-}X\text{-}Q^2\text{-}NR^3R^4 \qquad (1)$$

(wherein the symbols have the same meanings as those defined in the above (1)), which comprises reacting a compound of the formula (3):

$$Z\text{-}Q^1\text{-}X\text{-}Q^2\text{-}Z' \qquad (3)$$

(wherein $Q^1$, $X$ and $Q^2$ have the same meanings as those defined in the above (1), and $Z$ and $Z'$ are each the same or different and represent a leaving group), with a compound of the formula (4):

$$NHR^1R^2 \qquad (4)$$

(wherein $R^1$ and $R^2$ have the same meanings as defined in the above (1)), and

(16) a method for producing the complex compound described in any one of the above (10) to (12), characterized in that the ligand described in any one of the above (1) to (9) is contacted with a metal compound.

BEST MODE FOR CARRING OUT THE INVENTION

In the formulae described above, the alkylene group represented by $Q^3$ includes an alkylene group of 1 to 6 carbon atoms such as methylene, ethylene, propylene, and so on, and the said alkylene group may have substituent group(s), which may include an alkoxy group (for example, alkoxy of 1 to 6 carbon atoms such as methoxy, ethoxy, and so on), halogen atoms (for example, fluorine, chlorine, bromine, and so on). The number of the substituent(s) is preferably 1 to 5.

The cycloalkylene groups represented by $Q^3$ include cycloalkylene groups of 3 to 7 carbon atoms, such as cyclopropylene, cyclobutylene, cyclopentylene, cyclohexylene, and so on, and the said cycloalkylene groups may have substituent(s), including an alkoxy group (for example, alkoxy groups of 1 to 6 carbon atoms, such as methoxy, ethoxy, and so on), halogen atoms (for example, fluorine, chlorine, bromine, and so on). The number of the substituent(s) is preferably 1 to 5.

The arylene groups in the arylene groups represented by $Q^3$ which may be substituted include phenylene, naphthalenediyl, anthracenediyl, and so on, and the said substituent includes a straight-chain or branched-chain alkyl group of 1 to 6 carbon atoms (for example, methyl, ethyl, isopropyl, isobutyl and so on), the said alkoxy group, a hydroxy group, the said halogen atom and so on.

The divalent heterocyclic groups in the divalent heterocyclic groups represented by $Q^3$ which may be substituted are those formed by removing two hydrogen atoms from heterocyclic compounds, and preferable examples of such heterocyclic groups are, for example, five- or six-membered monocyclic aromatic heterocyclic compounds and polycyclic aromatic heterocyclic compounds. Such aromatic heterocyclic compounds include those (heterocyclic compounds) containing 4 to 14 carbon atoms and 1 to 3 hetero atoms such as nitrogen, oxygen, and sulfur atom. Specific examples of the said aromatic heterocyclic compounds include pyridine, imidazole, furan, pyrazine, benzofuran, and pyrrole and so on.

The substituents include the said alkyl groups, cycloalkyl groups (for example, cycloalkyl groups of 3 to 6 carbon atoms such as cyclopropyl, cyclobutyl, cyclohexyl and so on), halogenated alkyl groups (for example, halogenated alkyl groups which are formed from the said halogen atoms and the said alkyl groups), the said alkoxy groups and the said halogen atoms and so on. The number of the substituents present is preferably 1 to 5.

The alkyl groups in the alkyl groups represented by $R^5$ which may be substituted include, for example, alkyl groups of 1 to 6 carbon atoms, and the substituent includes, for example, cycloalkyl groups (for example, cycloalkyl groups of 3 to 6 carbon atoms, such as cyclopropyl, cyclobutyl, cyclohexyl, and so on), halogenated alkyl groups (for example, those halogenated alkyl groups which are formed from the said halogen atom and the said alkyl group), the said alkoxy groups, the said halogen atoms and so on.

The aryl groups in the aryl groups represented by $R^5$ which may be substituted include aryl groups of 6 to 14 carbon atoms. The specific examples of such aryl groups include a phenyl group, a naphthyl group, an anthryl group and so on.

The substituted aryl groups include aryl groups wherein at least one hydrogen atom is replaced by the said alkyl group, the said alkoxy group, the said halogen atom, nitro group, cyano group, and so on.

The heterocyclic groups represented by $R^5$ which may be substituted are preferably 5- or 6-membered monocyclic or polycyclic aromatic heterocyclic groups of 4 to 14 carbon atoms and 1 to 3 hetero atoms such as nitrogen atom, oxygen atom, sulfur atom and so on. Specific examples of such heterocyclic groups include pyridyl, imidazolyl, thiazolyl, pyranyl, furyl, benzofuryl, thienyl, pyrrolidonyl, piperidino, piperadinyl, morpholino, tetrahydrofuryl, tetrahydropyranyl and so on.

The metal atoms which may coordinate or bind to the substituent represented by $R^6$ are preferably those selected from 3 to 14 groups of the periodic table, and specific examples of such metal atoms include lanthanum, samarium, titanium, zirconium, vanadium, rhenium, iron, ruthenium, cobalt, rhodium, iridium, nickel, palladium, copper, zinc, aluminum, tin, gold, silver and platinum, and so on.

The substituents which may coordinate or bind to a metal atom include those containing, for example, one or more hetero atoms selected from the group consisting of O, N, P and S. Specific examples of those substituents include a hydroxy group, the said alkoxy group, an amino group, a substituted amino group (for example, a mono-substituted amino group such as methylamino and ethylamino, and a di-substituted amino group such as dimethylamino, diethylamino, morpholino), a phosphono group, a phosphino group, a substituted phosphono group (for example, diethylphosphono, dimethylphosphono, and diphenylphosphono), a substituted phosphino group, a mercapto group, and an alkylthio group (wherein the alkyl moiety has the same meaning as defined above).

The rings formed when $R^5$ and $R^6$ are taken together include a 5- or 6-membered ring having hetero atom(s) which may coordinate or bind to a metal atom. The said hetero atoms may either exist as a part of the atoms which constitute the substituents on the ring, or exist, when the ring is a heterocyclic one, as the atoms which constitute the heterocyclic group. These rings either may be substituted with the said alkyl group or aryl group, or may have asymmetric carbon atom(s). Specific examples of the ring structure include oxazoline, pyrroridine, piperidine and so on.

The divalent spacers represented by X are preferably an optionally substituted alkylene group, an optionally substituted arylene group or an optionally substituted divalent heterocyclic group, wherein these alkylene, arylene and divalent heterocyclic groups may be the same ones as those mentioned above, respectively. The length of $Q^1$-X-$Q^2$ is usually about 2-30 angstroms, preferably about 3 to 25 angstroms, and more preferably about 4 to 20 angstroms.

The optionally substituted alkylene groups represented by $Q^1$ and $Q^2$ include the same ones as those described above.

In the formula (2), one or more carbon atoms selected from the group consisting of the carbon atoms to which $Q^3$, $R^5$ and $R^6$ are attached, and the carbon atoms of $R^5$ and $R^6$ are preferably asymmetric carbon atoms.

The compounds of the formula (1) can be produced either according to the known procedures or the methods known per se, namely, for example, by reacting a compound of the formula (3):

$$Z-Q^1-X-Q^2-Z' \qquad (3)$$

(wherein $Q^1$, X and $Q^2$ have the same meanings as defined above, and Z and Z' are each the same or different and represent a leaving group), with a compound of the formula (4):

$$NHR^1R^2 \qquad (4)$$

wherein $R^1$ and $R^2$ have the same meanings as defined above.

The leaving groups represented by Z and Z' include, for example, a halogen atom, a trifluoromethanesulfonyloxy group, a p-toluenesulfonyloxy group, a methanesulfonyloxy group, and so on. In the reaction, the ratio of the compounds of the formulae (3) and (4) used is usually selected from a range of about 0.6 to 1.6 moles of the compound (4) to one mole of the compound (3). The reaction temperature is usually in the range of from about 20° C. to 200° C., and the reaction time is usually from about 5 minutes to 2 weeks. The reaction is preferably carried out in a solvent. Any solvent may be used if it does not inhibit the reaction. The reaction solvent specifically includes, for example, tetrahydrofuran, diethyl ether, benzene, xylene, chloroform, dichloromethane, and dimethylformamide, and so on. The reaction can be carried out preferably in the presence of a base such as trimethylamine, triethylamine, dimethylaniline, diethylaniline, pyridine, N,N,N'N'-tetramethylethylenediamine, methyl lithium, n-butyl lithium, sec-butyl lithium, tert-butyl lithium, phenyl lithium, lithium diisopropylamide, sodium methoxide, potassium tert-butoxide, potassium carbonate, and so on. The amount of the base used is usually in the range of about 2 to 100 moles, or more preferably about 2 to 50 moles, per one mole of the compound (3) used. After completion of the reaction, the reaction product may either be purified by subjecting it to the purifying procedures such as concentration, redissolution, extraction, crystallization, and chromatography, and so on, or may be subjected directly to the reaction with a metal atom.

The compounds of the formula (1) can also be produced by introducing the above groups $R^1$, $R^2$, $R^3$ and $R^4$ onto the four hydrogen atoms of the two amino groups of the compound (5):

$$H_2N-Q^1-X-Q^2-NH_2 \qquad (5)$$

wherein $Q^1$, X and $Q^2$ have the same meanings as described above. Since methods for introducing the said substituents onto the amino groups have already been established well, those known methods may be adopted in the present invention, too.

The compounds of the formula (1) thus obtained may either be used as they are, as a catalyst component in the various asymmetric synthesis reactions described below, or the complex compounds which are prepared by bringing the compound of the formula (1) into contact with the metal compound may be used as a catalyst for asymmetric synthesis reactions.

The said complex compounds can be produced by reacting the compound of the formula (1) with a metal compound. A great number of metal compounds for the production of the complex compounds have so far been known in the field of the art, and those known metal compounds may be conveniently used also in the present invention. Although there is no particular limitation to the metal compounds, such metal compounds include, for example, metal-halides (for example, chloride, bromide, iodide and so on), metal-carbonyl compounds, metal-carbonyl compounds combined with oxidants (for example, iodine, bromine, diiodomethane, diiodoethane and so on), metal-organic acid salts (for example, carboxylic acid salts such as acetate, trifluoroacetate and so on, and sulfonic acid salts such as methanesulfonate, trifluoromethanesulfonate and so on), metal-organic acid derivative salts (for example, salts of organic acid amides such as acetylamide, formamide, benzamide and so on), metal-inorganic acid salts (for example, sulfates, nitrates, perchlorates, phosphates and so on), metal-cyclic alkene compounds (for example, cyclooctadiene, cyclooctene, norbornadiene and so on), and metal compounds having a ligand (for example, hydroxy group, alkyl group, aryl group, alkoxy group, aryloxy group, amino group, cyano group, and thiolate group) which may coordinate to a metal. Among these metal compounds, metal-halaides, metal-organic acid salts, metal-inorganic acid salts and metal-alkoxides are used more preferably. The amount of the metal compounds used is within the range of about 1 to 4 moles, or more preferably about 1.5 to 3 moles per 1 mole of the compound of the formula (1), though there is no particular limitation to such amount. The reaction temperature is usually in the range of about −10° C. to 250° C., and the reaction time is usually in the range of about 5 minutes to 10 days. The reaction is preferably carried out in a solvent. There is no limitation to the solvent to be used, so far as the solvent makes it possible for the reaction to proceed smoothly without inhibiting the reaction. Specific examples of the reaction solvent include, for example, acetone, methyl ethyl ketone, heptane, pentane, methanol, ethanol, tetrahydrofuran, diethyl ether, benzene, xylene, chloroform, dichloromethane and dimethylformamide. After completion of the reaction, the reaction product may either be purified by subjecting it to various purification procedures such as concentration, redissolution, extraction, crystallization, and chromatography, and so on, or may be used as it is and served as a catalyst for asymmetric synthetic reactions.

Some specific examples of the said metal compounds are given below concerning about some of the metals described above, although it is quite obvious that the metal compounds of the present invention are not restricted to these examples. Each of the symbols used in the chemical formulae of the metal compounds shown below has the following meaning: x is an integer, dba is dibenzylideneacetone, Ac is acetyl, acac is acetylacetonato, cod is 1,5-cyclooctadiene, coe is cyclooctene, Tf is trifluoromethanesulfonyl ($SO_2CF_3$), nbd is norbornadiene, Ph is phenyl, arene is one of benzene, mesitylene, p-cymene and hexamethylbenzene, Me is methyl, and Et is ethyl.

Examples of the samarium compound include, for example, $SmCl_2$, $SmCl_3$, $SmBr_2$, $SmBr_3$, $SmI_2$, $SmI_3$, $Sm(O-CH(CH_3)_2)_3$, $Sm(NO_3)_3$, $Sm(OAc)_3 \cdot xH_2O$, and so on.

Examples of the titanium compound include, for example, $TiCl_4$, $TiBr_4$, $TiI_4$, and $Ti(OCH(CH_3)_2)_4$, and so on.

Examples of the palladium compound include, for example, $Pd(dba)_2$, $Pd(dba)_3$, $Pd_2(dba)_3$, $Pd(PPh_3)_4$, $PdCl_2$, $PdBr_2$, $PdI_2$, $Pd(OAc)_2$, $PdCl_2(CH_3CN)_2$, $PdCl_2(PhCN)_2$, $[PdCl(\pi\text{-allyl})]_2$, $[PdCl(2\text{-methylallyl})]_2$, $Pd(acac)_2$, and so on.

Examples of the nickel compound include, for example, $Ni(cod)_2$, $NiCl_2$, $NiBr_2$, $NiI_2$, and so on.

Examples of the copper compound include, for example, $CuCl_2$, $CuBr_2$, $CuI_2$, $Cu(OCH_3)_2$, $Cu(NO_3)_2 \cdot xH_2O$, $Cu(OTf)_2$, $Cu(OAc)_2$, $Cu(acac)_2$, $Cu(CF_3CO_2)_2$, and so on.

Examples of the iron compound include, for example, $FeCl_2$, $FeBr_2$, $FeI_2$, $FeCl_3$, $FeBr_3$, $FeI_3$, $Fe_2(CO)_9$, $Fe_3(CO)_{12}$, $(NH_4)_4Fe(CN)_6$, $(NH_4)_4Fe(SO_4)_2 \cdot 6H_2O$, $Fe(NO_3)_3 \cdot 9H_2O$, $Fe(ClO_4)_3 \cdot xH_2O$, $Fe(BF_4)_2 \cdot 6H_2O$, $K_3Fe(CN)_6$, and so on.

Examples of the rhodium compound include, for example, $RhCl_3$, $RhCl_3 \cdot xH_2O$, $RhBr_3 \cdot xH_2O$, $RhI_3 \cdot xH_2O$, $[Rh(OAc)_2]_2$, $[Rh(C_7H_{15}CO_2)_2]_2$, $[Rh(CF_3CO_2)_2]_2$, $Rh(acac)_3$, $Rh(acac)(CO)_2$, $[RhCl(cod)]_2$, $[RhCl(nbd)]_2$, $[RhCl(C_2H_4)]_2$, $[Rh(cod)_2]BF_4$, $[Rh(cod)_2]OTf$, $[Rh(cod)_2]ClO_4$, $[Rh(cod)_2]PF_6$, $[Rh(cod)_2]BPh_4$, $[Rh(nbd)_2]BF_4$, $[Rh(nbd)_2]OTf$, $[Rh(nbd)_2]ClO_4$, $[Rh(nbd)_2]PF_6$, $[Rh(nbd)_2]BPh_4$, $Rh_6(CO)_{16}$, $Rh_4(CO)_{12}$, and so on.

Examples of the ruthenium compound include, for example, $RuCl_3$, $RuCl_3 \cdot xH_2O$, $RuBr_3 \cdot xH_2O$, $RuI_3$, $RuI_3 \cdot xH_2O$, $[RuCl_2(cod)]_x$, $[RuCl_2(arene)]_2$, $[RuBr_2(arene)]_2$, $[RuI_2(arene)]_2$, $Ru(acac)_3$, $Ru_3(CO)_{12}$, and so on.

Examples of the iridium compound include, for example, $IrCl_3 \cdot xH_2O$, $IrCl_4 \cdot xH_2O$, $IrBr_3 \cdot xH_2O$, $[IrCl(cod)]_2$, $[IrBr(cod)]_2$, $[IrI(cod)]_2$, $[IrCl(coe)_2]_2$, $[Ir(cod)_2]BF_4$, $Ir(cod)(acac)$, $[Ir(cod)(CH_3CN)_2]BF_4$, $Ir_4(CO)_{12}$, $[IrCl(CO)_3]_x$ and so on.

Examples of the zinc compound include, for example, $ZnCl_2$, $ZnBr_2$, $ZnI_2$, $Me_2Zn$, $Et_2Zn$, $Ph_2Zn$, $Zn(OAc)_2 \cdot 2H_2O$, $Zn(acac)_2 \cdot xH_2O$, $Zn(NO_3)_2$, $Zn(ClO_4)_2$, $Zn_3(PO_4)_2$, and so on.

Examples of the tin compound include, for example, $Me_2SnO$, $Et_2SnO$, $(n\text{-}C_3H_7)_2SnO$, $(n\text{-}C_4H_9)_2SnO$, $(n\text{-}C_8H_{17})_2SnO$, $(n\text{-}C_{12}H_{25})_2SnO$, $(PhCH_2)_2SnO$, $Ph_2SnO$, $(4\text{-}Cl\text{-}C_6H_4)_2SnO$, $(4\text{-}MeO\text{-}C_6H_4)_2SnO$, $(1\text{-}C_{10}H_7)_2SnO$ (di-(1-naphthyl)tinoxide), $(2\text{-}C_{10}H_7)_2SnO$ (di-(2-naphthyl)tinoxide), and so on.

Examples of the gold compound include, for example, $AuCl$, $AuBr$, $AuI$, $AuCl_3$, $AuBr_3$, $AuI_3$, $Au(CO)Cl$, $AuCN$, $Me_2Au(acac)$, $KAu(CN)_2$, $NaAu(CN)_2$, $Au(OH)_3$, $HAuCl_4$, $HAuBr_4$, $KAuCl_4$, $KAuBr_4$, and so on.

Examples of the silver compound include, for example, $AgCl$, $AgBr$, $AgI$, $AgNO_3$, $AgSbF_6$, $AgBF_4$, $AgCN$, $Ag(OAc)$, $KAg(CN)_2$, $Ag(PhCO_2)$, $Ag(acac)$, $AgClO_4$, $AgPF_6$, $Ag_3PO_4$, and so on.

Examples of the platinum compound include, for example, $PtCl_2$, $PtBr_2$, $PtI_2$, $PtCl_4$, $PtBr_4$, $K_2PtCl_4$, $K_2PtBr_4$, $K_2PtI_4$, $K_2Pt(CN)_4$, $H_2PtCl_6$, $H_2PtBr_6$, $K_2PtCl_6$, $K_2PtBr_6$, $K_2PtI_6$, $K_2Pt(CN)_6$, $H_2Pt(OH)_6$, $Pt(CN)_2$, $PtCl_2(cod)$, $PtBr_2(cod)$, $PtI_2(cod)$, $Pt(acac)_2$, $PtCl_2(PhCN)$, $PtCl_2(CH_3CN)$, $Me_2Pt(cod)$, $PtCl_2(C_5H_5N)_2$, $PtCl_2(NH_2CH_2CH_2NH_2)_2$, $(NH_3)_2PtCl_4$, $(NH_3)_2PtCl_6$, $(NH_3)_2PtBr_6$, and so on.

The complex compounds thus obtained can be used as a catalyst in various reactions. Typical example of such reactions is asymmetric syntheses. Examples of such asymmetric syntheses include, for example, asymmetric hydrogenation, asymmetric transfer hydrogenation, asymmetric hydrosilylation, asymmetric Heck reaction, asymmetric aldol reaction, asymmetric ene reaction, asymmetric oxidation, asymmetric epoxidation, asymmetric Diels-Alder reaction, polymerization, and so on. Specific examples of such reactions include, for example, the Meerwein-Ponndorf-Verley reduction which is used, for example, for producing optically active alcohols from ketones.

EXAMPLES

Hereinafter, the present invention will be explained in more detail by way of Examples. However, the present invention is in no way limited to these Examples. In the Examples, the following analytical apparatuses were used: MERCURY300-C/H (Varian) $^1$H-NMR (300.09 MHz) for nuclear magnetic resonance spectrum measurement, and Gulliver(JASCO Corp.) for high performance liquid chromatography (HPLC).

Example 1

Synthesis of 1,3-bis[N,N-di((2R)-2-hydroxy-2-phenylethyl)aminomethyl]-benzene (a ligand)

m-Xylylenediamine (1 ml, 7.84 mmol) was dissolved in ethanol (2 ml). To the stirred solution was added a solution of (R)-(+)-styrene oxide (3.6 ml, 31.3 mmol) dissolved in ethanol (4 ml), under cooling to 0° C. After being kept at 0° C. for one hour, the reaction mixture was heated up and refluxed for 20 hours. The resulting reaction solution was purified by a silica-gel column chromatography with hexane/ethyl acetate=3/1 to give a yellow oil (2.3536 g, 3.81 mmol, 49% yield).

$^1$H-NMR(CDCl$_3$, 35° C.) δ: 7.32-7.18(m, 24H, phenyl protons), 4.73(dd, J=9.75, 3.43 Hz, 4H, —CH$_2$—CH(OH)—Ph), 3.99(d, J=13.46 Hz, 2H, Ph-CHH—N—), 3.71(d, J=13.46 Hz, 2H, Ph-CHH—N—), 2.83(dd, J=13.32, 9.75 Hz, 4H, —N—CHH—CH(OH)Ph), 2.74(dd, J=13.32, 3.43 Hz, 4H, —N—CHH—CH(OH)Ph).

The compound described above is shown by the following formula:

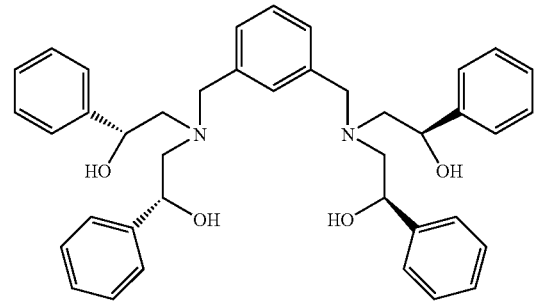

Example 2

Synthesis of 1,3-bis[N,N-di{(2R)-2-hydroxy-2-phenylethyl}aminomethyl]-2-hydroxy-5-methylbenzene (a ligand)

(1) Synthesis of (1R,5R)-3-aza-1,5-dihydroxy-1,5-diphenylpentane

In an atmosphere of argon, (1R,5R)-3-aza-3-benzyl-1,5-dihydroxy-1,5-diphenylpentane (0.6825 g, 1.96 mmol), Pd/C (10 wt % to the substrate) and methanol (10 ml) were placed in an autoclave. Then, the mixture was stirred at room temperature for 2 days under a hydrogen pressure of 7 MPa. After removal of the Pd/C by filtration, the solvent was evaporated off to give a yellow oil (0.4015 g, 1.56 mmol, 80% yield).

$^1$H-NMR(CDCl$_3$, 35° C.) δ: 7.35-7.18 (m, 10H, phenyl protons), 4.77 (dd, J=12.29, 3.99 Hz, 2H, —CH$_2$—CH(OH)—Ph), 2.93 (dd, J=12.29, 8.52 Hz, 2H, —N—CHH—CH(OH)Ph), 2.85(dd, J=8.52, 3.99 Hz, 2H, —N—CHH—CH(OH)Ph).

(2) Synthesis of the Ligand 2,6-Bis(hydroxymethyl)-p-cresol (0.6779 g, 4.03 mmol) was suspended in CH$_2$Cl$_2$ (10 ml), and to this suspension was added slowly SOCl$_2$ (3 ml, 41.1 mmol) under cooling in an ice-bath, and the resulting mixture was stirred at room temperature for 18 hours. The color of the reaction solution turned yellow. After completion of the reaction, the solvent was removed by evaporation to give 2,6-bis(chloromethyl)-p-cresol.

2,6-Bis(chloromethyl)-p-cresol (0.0368 g, 0.178 mmol) and (1R,5R)-3-aza-1,5-dihydroxy-1,5-diphenylpentane (0.0953 g, 0.370 mmol) were dissolved in methanol (5 ml). After addition of triethylamine (1 ml) thereto, the mixture was stirred overnight at room temperature. The reaction solution was filtered through a glass filter, and the solvent in the filtrate was evaporated off to give a yellow oil (0.0852 g, 74% yield).

$^1$H-NMR(CDCl$_3$, 35° C.) δ: 7.20-7.32(m, 22H, phenyl protons), 4.83(dd, J=3.02, 10.37 Hz, 4H, —CH—OH), 4.14(d, J=13.04 Hz, 2H, C$_6$H$_2$—(CHH)$_2$—), 3.65(d,J=13.04 Hz, 2H, C$_6$H$_2$—(CHH)$_2$—), 2.83(dd, J=10.37, 13.19 Hz, 4H, —CH$_2$—N—(CHH—)$_2$), 2.68(dd, J=3.02, 13.19 Hz, 4H, —CH$_2$—N—(CHH—)$_2$), 2.28(s, 3H, —CH$_3$).

The compound described above is shown by the following formula:

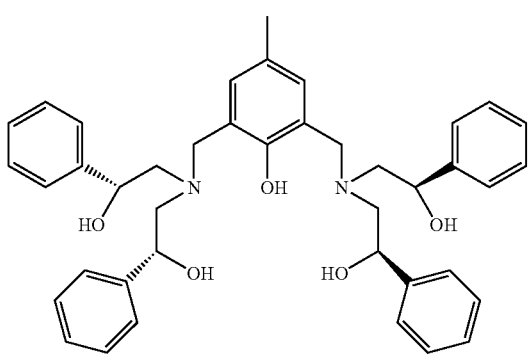

Example 3

Synthesis of a Samarium Catalyst and an Asymmetric Hydrogen Transfer Type Reaction (1) In an argon atmosphere, the compound obtained in Example 1 (0.1505 g, 244 μmol) was placed in a Schlenk glassware, and tetrahydrofuran (2 ml) was added thereto. A n-BuLi (n-butyl lithium) hexane solution (0.73 ml, 1.34 M 978 μmol) was added slowly at 0° C. to the mixture by means of a syringe. The color of the reaction solution turned red.

(2) In an argon atmosphere, metallic samarium (0.0736 g, 489 μmol) was suspended in tetrahydrofuran (2 ml) in a Schlenk glassware, and diiodoethane (0.2065 g, 732 μmol) was added to the suspension, followed by stirring at room temperature for 1 hour. The color of the reaction solution changed from green to yellow.

(3) The reaction solution obtained in (1) was added dropwise to the reaction solution obtained in (2) at room temperature by means of a syringe. The reaction solution turned a yellow brown color, indicating that a samarium catalyst was formed in the reaction solution.

(4) To the reaction solution obtained in (3) were added acetophenone (0.56 ml, 4.81 mmol) and 2-propanol (9.4 ml, 121 mmol), and the mixture was stirred at 25° C. for 24 hours. The reaction mixture was purified by means of Kugelrohr distillation to give (R)-1-phenylethanol (0.541 g, 92% yield). The asymmetric yield of the product was measured in a HPLC using a CHIRALCEL OD column (4.6×250 mm, Daicel Chemical Industries Ltd) and found to be not less than 99% e.e. In the table below, the results obtained by using a metal-ligand complex 4 (described on page 9800 of J. Am. Chem. Soc. 1993, 115, 9800-9801 and hereinafter referred to as the comparative compound) are also given for comparison.

TABLE 1

| Catalyst | Yield | Asymmetric yield e.e. |
|---|---|---|
| The samarium catalyst in Example 3-(3)(footnote 1) | 92% | >99% e.e. |
| The comparative compound (footnote 2) | 83% | 96% e.e. |

Footnote 1: The structure of the samarium catalyst:

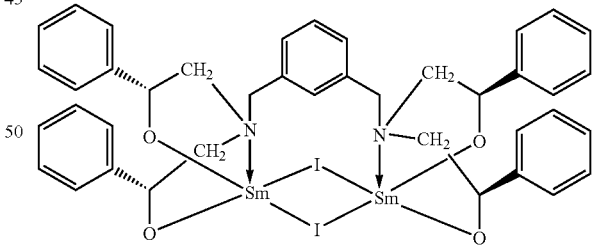

Footnote 2: The structure of the comparative compound:

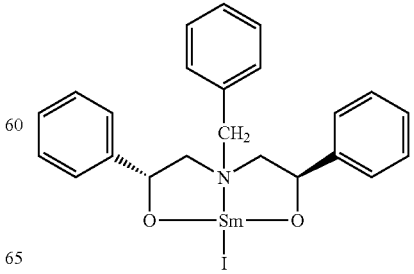

Table 1 shown above reveals that the objective optically active alcohol can be produced in a high chemical yield and in a very high asymmetric yield, and thus the complex compound of the present invention exhibits excellent catalytic ability.

Example 4

Synthesis of 1,3-bis[N,N-di{4,5-dihydro-4(R)-phenyl-1,3-oxazol-2-ylmethyl}aminomethyl]benzene (a ligand)

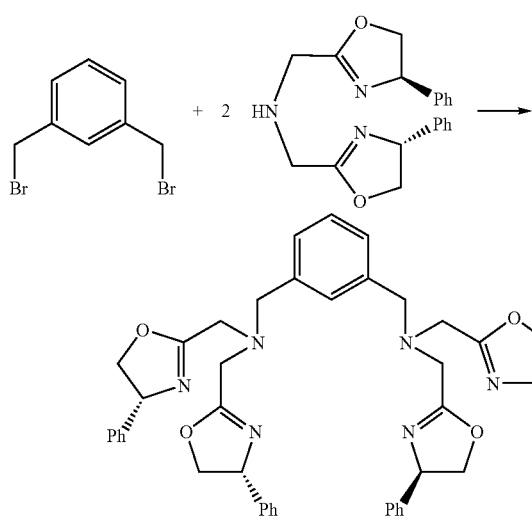

N,N-Di[4,5-dihydro-4(R)-phenyl-1,3-oxazol-2-ylmethyl]amine (synthesized according to the description by Jiang, Y., J. Am. Chem. Soc., 1998, 120, 3817.) (196.3 mg, 58.5 μmol) was dissolved in methanol (1 ml) in a 20-ml Schlenk glassware. To this solution were added triethylamine (0.13 ml, 57.3 μmol) and α,α'-dibromo-m-xylene (0.04 ml, 27.4 μmol), and the mixture was stirred at room temperature for 40 hours. After removal of the solvent by evaporation, the residue was purified by a silica gel column chromatography (hexane:ethyl acetate=1:3 (by volume) and 3% by volume of triethylamine) to give the title compound (81.7 mg) as a brown oil. The yield was 30%.

$^1$H-NMR (300 MHz, CDCl$_3$, 35° C.) δ: 7.43-7.20 (m, 24H, phenyl protons), 5.21(dd, J=9.9, 14.8 Hz, 4H, —CH—CH$_2$—O—), 4.60(dd, J=9.9, 8.5 Hz, 4H, —CHH—CH-Ph), 4.11(dd, J=14.8, 8.5 Hz, 4H, —CHH—CH—Ph), 3.99(s, 4H, Ar—CH$_2$—N—), 3.71(s, 8H, —N—CH$_2$—C).

MS (FAB): m/z 773.

HRMS (FAB): Found 773.9582, Calcd. 773.9549.

Example 5

Synthesis of 1,3-bis[N,N-di{4,5-dihydro-4(S)-isopropyl-1,3-oxazol-2-ylmethyl}aminomethyl]benzene (a ligand)

N,N-Di[4,5-dihydro-4(S)-isopropyl-1,3-oxazol-2-yl-methyl]amine (396.1 mg, 1.48 mmol) was dissolved in methanol (1 ml) in a 20-ml Schlenk glassware. To this solution were added triethylamine (0.2 ml, 1.43 mmol) and α,α'-dichloro-m-xylene (0.07 ml, 480 μmol), and the mixture was stirred at room temperature for 16 hours. The solvent was removed by evaporation and the residue was purified by a silica gel column chromatography (hexane ethyl acetate=2:5 (by volume) and 3% by volume of triethylamine) to give the title compound as a brown oil (149.9 mg). The yield was 49%.

$^1$H-NMR (300 MHz, CDCl$_3$, 35° C.) d: 7.42-7.25 (m, 4H, phenyl protons), 4.22(dd, J=8.2, 7.2 Hz, 4H, —CH—CHH—), 3.95(dd, J=13.8, 7.2 Hz, 4H, —CH—CHH—), 3.90-3.88(m, 4H, —CH—CHH—), 3.85(s, 4H, Ar—CH$_2$—N—), 3.51(s, 4H, —NH—CH$_2$—). 1.75(d, septet, J=6.6, 6.6 Hz, 2H, CH$_3$—CH—CH$_3$), 0.97(d, J=6.6 Hz, 6H, CH$_3$—CH—CH$_3$), 0.88(d, J=6.6 Hz, 6H, CH$_3$—CH—CH$_3$).

Example 6

Synthesis of 1,3-bis[{(2S,6S)-1,7-di(trifluoromethanesulfonyl)-2,6-diisopropyl-1,4,7-triazaheptan-4-yl}methyl]benzene (a ligand).

(1) Synthesis of (R)-N-trifluoromethanesulfonyl-2-isopropylaziridine (5)

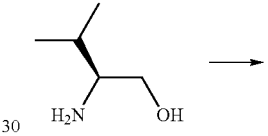

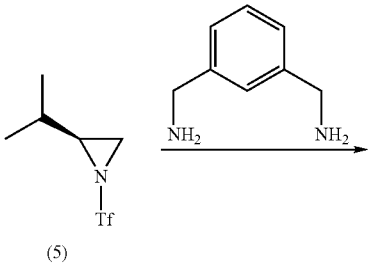

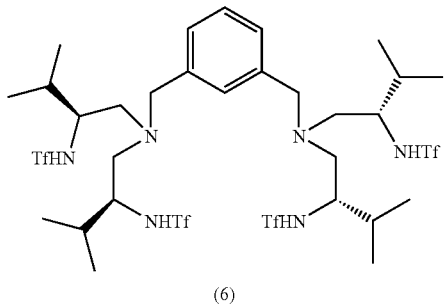

According to the method by Cernerud, M. et al., (Tetrahedron: Asymmetry, 1997, 15, 2655), aziridine (5) was synthesized. What follows is the detailed description of this synthesis.

In an atmosphere of argon, L-valinol (2.4 ml, 21.5 mmol) was dissolved in methylene chloride (40 ml) and triethylamine (5.6 ml, 40.1 mmol) in an 80-ml Schlenk glassware. The resulting solution was cooled to −78° C. Then, trifluoromethanesulfonic anhydride (7.2 ml, 33.7 mmol) was added slowly to the solution with the aid of a dropping funnel. The temperature was raised to −30° C., and the resulting mixture was stirred at −30° C. overnight. The reaction solution was washed successively with 1M hydrochloric acid (twice, with 50 ml each) and aqueous saturated sodium bicarbonate solution (twice, with 50 ml each), and dried over anhydrous magnesium sulfate. The solvent was removed by evaporation to give 3.1307 g of (R)—N-trifluoromethanesulfonyl-2-isopropylaziridine (5) as a brown oil. The yield was 67%.

(2) Synthesis of the ligand (6)

According to the method by Cernerud, M. et al., (Tetrahedron: Asymmetry, 1997, 20, 3437.), the compound (6) was synthesized as follows.

(R)—N-Trifluoromethanesulfonyl-2-isopropylaziridine (5) (3.1307 g) was dissolved in methanol (2 ml). To this solution was added m-xylenediamine (0.31 ml, 2.34 mmol), and the mixture was stirred at 60° C. for 2 days, followed by a silica gel chromatography (ethyl acetate:hexane=1:4 (by volume)) to give a ligand (6) (1.0492 g) as a colorless solid. The yield was 45%.

$^1$H-NMR(300 MHz, CDCl$_3$, 35° C.) d: 7.49-7.20 (m, 4H, phenyl protons), 3.91(d, J=13.5 Hz, 4H, Ar—C$\underline{H}_2$—N—), 3.53(m, 4H, N—CHH—C$\underline{H}$—), 2.67(dd, J=13.5, 9.6 Hz, 4H, N—CHH—C$\underline{H}$—), 2.51(dd, J=13.5, 5.1 Hz, 4H, —N—CH $\underline{H}$—CH—), 1.97(m, 4H, CH$_3$—C$\underline{H}$—CH$_3$), 0.90(d, J=7.0 Hz, 12H, CH$_3$—CH—C$\underline{H}_3$), 0.86(d, J=7.0 Hz, 12H, C$\underline{H}_3$—CH—CH$_3$).

[α]$_D$ −71.9° (c 1.0, CH$_3$OH).

MS(FAB): m/z 1005.

HRMS(FAB): Found 1006.0491, Calcd. 1006.0531.

Melting point: 196-201° C.

Example 7

Synthesis of (S)-4-isobutyl-2-oxetanone

In an atmosphere of argon, the ligand (6) obtained in Example 6 (0.10 g, 0.10 mmol) was suspended in methylene chloride (5 ml) in a Schlenk glassware, and to this suspension was added trimethylaluminum in toluene (0.20 ml of 1M solution, 0.20 mmol) via a syringe. Then, the resulting mixture was stirred at room temperature for 3 hours. The reaction mixture changed from a white suspension into a colorless solution. After completion of the stirring, the solvent was removed by evaporation under reduced pressure. Hexane (5 ml) was added to the residue, and the mixture was further stirred for one hour. After that, the mixture was allowed to stand for a while, and the supernatant liquid was removed by means of a syringe. The precipitate was dried under reduced pressure to give a catalyst. To the catalyst obtained was added methylene chloride (16 ml), followed by the addition of N,N-diisopropylethylamine (0.59 ml, 3.4 mmol). The mixture was cooled to −78° C. in a dry ice-ethanol bath. To this were added acetyl bromide (0.28 ml, 3.8 mmol) and isovaleraldehyde (0.21 ml, 2.0 mmol) via a syringe, and the mixture was stirred at −50° C. for 24 hours, during which time the reaction solution turned pale yellow. After completion of the reaction, the reaction mixture changed to orange when it was warmed up to room temperature. The reaction mixture was filtered through a glass filter packed with silica gel, and the solvent of the filtrate was evaporated off to give (S)-4-isobutyl-2-oxetanone (0.20 g, 77% yield). The asymmetric yield of the product was measured by means of GLC using a capillary column Chira-sil-DEX CB (0.25 mm×25 m, membrane thickness 0.25 μm, GL Science) and was found to be 93% e.e.

INDUSTRIAL APPLICABILITY

Complex compounds produced by using the ligand of the present invention are useful as a catalyst for asymmetric syntheses and extremely useful from industrial viewpoint.

The invention claimed is:

1. An optically active ligand represented by the formula (1):

$$R^1R^2N-Q^1-X-Q^2-NR^3R^4 \quad (1)$$

wherein $R^1$, $R^2$, $R^3$ and $R^4$ are each the same or different and represent a group represented by the formula (2):

(2)

wherein $Q^3$ is an optionally substituted alkylene group, an optionally substituted cycloalkylene group, an optionally substituted arylene group or an optionally substituted divalent heterocyclic group; $R^5$ is an optionally substituted alkyl group, an optionally substituted aryl group or an optionally substituted heterocyclic group; and $R^6$ is a substituent which may coordinate or bind to a metal atom, or $R^5$ and $R^6$, taken together, may form a ring, $Q^1$ and $Q^2$ are each the same or different and represent an optionally substituted alkylene group or a single bond, and X is a divalent spacer.

2. The ligand according to claim 1, wherein the spacer is an optionally substituted alkylene group, an optionally substituted arylene group or an optionally substituted divalent heterocyclic group.

3. The ligand according to claim 1, wherein the length of $Q^1$-X-$Q^2$ is from 2 to 30 angstroms.

4. The ligand according to claim 1, wherein $Q^3$ is an alkylene group of 1 to 6 carbon atoms.

5. The ligand according to claim 1, wherein $R^5$ is an aryl group.

6. The ligand according to claim 1 characterized in that-wherein $R^6$ is a hydroxy group, an alkoxy group of 1 to 6 carbon atoms, an amino group or a substituted amino group.

7. The ligand according to claim 1, wherein the ring formed when $R^5$ and $R^6$ are taken together is an oxazoline, a pyrrolidine or a piperidine.

8. A complex compound comprising, as a constituent element, the ligand according to claim 1 and a metal atom.

9. The complex compound according to claim 8, wherein the metal atom belongs to any one of groups 3 to 14 of the periodic table.

10. The complex compound according to claim 8, wherein the metal atom is selected from the group consisting of lanthanum, samarium, titanium, zirconium, vanadium, rhenium, iron, ruthenium, cobalt, rhodium, iridium, nickel, palladium, copper, zinc, aluminum, tin, gold, silver and platinum.

11. A method for producing a an optically active compound of the formula (1):

$$R^1R^2N-Q^1-X-Q^2-NR^3R^4 \quad (1)$$

wherein the symbols have the same meanings as defined in claim 1, which comprises reacting a compound of the formula (3):

$$Z-Q^1-X-Q^2-Z' \quad (3)$$

wherein $Q^1$, X and $Q^2$ have the same meanings as defined in claim 1, and Z and Z' are each the same or different and represent a leaving group, with a compound of the formula (4):

$$NHR^1R^2 \quad (4)$$

wherein $R^1$ and $R^2$ have the same meanings as defined in claim 1.

12. A method for producing a complex compound, which comprises contacting the ligand described in claim 1 with a metal compound.

13. The method according to claim 12, wherein the metal compound comprises a metal atom selected from the group consisting of lanthanum, samarium, titanium, zirconium, vanadium, rhenium, iron, ruthenium, cobalt, rhodium, iridium, nickel, palladium, copper, zinc, aluminum, tin, gold, silver and platinum.

14. A method for catalyzing an asymmetric synthesis reaction, which comprises adding the complex compound according to claim 8 as a catalyst to an asymmetric synthesis reaction.

* * * * *